| United States Patent [19] | [11] Patent Number: 4,710,524 |
| Donohue | [45] Date of Patent: Dec. 1, 1987 |

[54] HIGH ENERGY RADIATION STABILIZATION OF SEMI-CRYSTALLINE POLYMERS

[75] Inventor: John Donohue, New York, N.Y.

[73] Assignee: Becton, Dickinson and Company, Franklin Lakes, N.J.

[21] Appl. No.: 762,600

[22] Filed: Aug. 5, 1985

Related U.S. Application Data

[63] Continuation-in-part of Ser. No. 545,578, Oct. 26, 1983, abandoned.

[51] Int. Cl.$^4$ .............................................. C08J 3/28
[52] U.S. Cl. ...................................... 522/75; 522/78; 522/83; 604/187; 524/99
[58] Field of Search .................... 524/99; 604/187; 522/75, 78, 83

[56] References Cited

U.S. PATENT DOCUMENTS

| | | | |
|---|---|---|---|
| 3,546,161 | 12/1970 | Wolheim | 260/45.85 |
| 3,940,325 | 2/1976 | Hirao | 204/159.17 |
| 4,110,185 | 8/1978 | Williams et al. | 204/159.2 |
| 4,274,932 | 6/1981 | Williams et al. | 204/159.2 |
| 4,314,933 | 2/1982 | Berner | 428/416 |
| 4,344,876 | 8/1982 | Berner | 524/91 |
| 4,369,274 | 6/1983 | Thomas | 524/99 |
| 4,450,248 | 5/1984 | Leistner et al. | 524/99 |
| 4,546,148 | 10/1985 | Cantatore | 524/99 |
| 4,563,259 | 1/1986 | Rayner | 524/99 |

OTHER PUBLICATIONS

Carssen et al., *Journal of Applied Polymer Science*, vol. 16, pp. 615-626, 1972.
Tozzi et al., *Textile Research Journal*, vol. 48, 1978.
Allen et al., *Journal of Applied Polymer Science*, vol. 27, pp. 2761-2772, 1982.

*Primary Examiner*—Allan M. Lieberman
*Attorney, Agent, or Firm*—Richard E. Brown

[57] ABSTRACT

A radiation stabilized and sterilized, flexible article is comprised of a semi-crystalline polymer having a crystalline content of from twenty percent to ninety percent. This polymer has been irradiated with a sterilizing amount of high energy radiation while having incorporated therein radiation stabilizing amounts of a hindered piperidine compound a benzophenone precursor sufficient to render the article substantially resistant to radiolysis while retaining its flexibility.

A method for sterilizing and radiation stabilizing a semi-crystalline polymer is also part of the present invention.

21 Claims, No Drawings

HIGH ENERGY RADIATION STABILIZATION OF SEMI-CRYSTALLINE POLYMERS

This application is a continuation-in-part application of Ser. No. 545,578, filed on Oct. 26, 1983, now abandoned.

BACKGROUND OF THE INVENTION

1. Field of the Invention

The present invention relates to high energy radiation stabilized, irradiated polymeric materials and the method for producing same, and more particularly, concerns a radiation stabilized and sterilized, flexible, non-disclored, semi-crystalline polymer and the method for producing same.

2. Description of the Prior Art

Semi-crystalline polymeric materials, including the polyolefins of which polypropylene is most significant with respect to the present invention, are often employed in producing articles subsequently subjected to irradiation sterilization techniques. For example, in the health and medical field, these sterilizable articles include syringes, tubing and tube assemblies, microbiological plastics, flasks, package film and the like. It is well-known that these semi-crystalline polymeric materials, if not properly stabilized, will discolor and become embrittled after exposure to high energy radiation at levels above 0.1 megarads.

After irradiation has been completed, post-irradiative oxidative degradation has only begun. Free radicals trapped in the crystalline regions of the polymeric materials slowly discharge into the amorphous regions where the bulk of their participation in the branching chain reactions of radiation induced free radical degradation occurs. Therefore, degradation of the mechanical properties of these polymeric materials, such as polypropylene, may not be obvious immediately following irradiation, but as time goes on, brittleness becomes more and more pronounced. Since many medical products made of semi-crystalline polymeric material are subjected to high energy radiation for sterilization purposes, the search goes on to develop satisfactory stabilizers which will render these materials nearly impervious to radiation damage in the region of 0.5 to 6 megarads or somewhat higher, while not imparting unacceptable discoloration to the materials.

Some recent attempts have been made to improve the stability of semi-crystalline polymeric materials so as to reduce embrittlement. For example, U.S. Pat. Nos. 4,110,185 and 4,274,932 disclose flexible, sterilized articles comprised of semi-crystalline polymer which have been irradiated with a sterilizing amount of high energy radiation. Both of these patented inventions, however, rely on the inclusion in the polymer of a mobilizing amount of non-crystalline mobilizing additive. While these materials represent significant improvements, particularly with respect to the embrittlement problem, the inclusion of the mobilizing additive, preferably a hydrocarbon oil, produces some undesirable side effects. In particular, use of oil as the mobilizing additive sometimes causes handling problems, and if the final product is a syringe or the like which usually has graduation marks thereon, the imprinting step is rendered difficult due to the oil in the polymeric material. Thus, while the materials of the aforementioned patents improve or maintain the flexibility of the polymeric material after high energy irradiation, elimination of the undesirable side effects would be welcomed by the manufacturers or users of these materials.

Using stabilizers to protect polyolefins from thermooxidation and photo-oxidation has been known and reported in the literature. For example, Tozzi et al., in "Recent Progress in the Stabilization of Polypropylene Fibers," *Textile Research Journal,* volume 48, pages 433–436, 1978, describe two new light stabilizers of the hindered amine type for the light stabilization of polypropylene multifilaments. Tozzi et al. suggested that hindered amines apparently do not act directly as radical scavengers, but that the active compounds are the very stable N-oxyl radicals formed by the oxidation of the amine by peroxy radicals or by singlet oxygen. Thus, Tozzi et al. felt that the stabilizing action of these radicals appears to be due to their capacity to trap the less stable radicals formed in the polymer as a result of irradiation and post-irradiative oxidation, with regeneration of N-oxyl radicals and final formation of inactive compounds.

Discoloration and radiolysis of polymeric materials, such as the polyolefins, as a result of high energy radiation is still being investigated not only to completely understand its mechanism, but also to determine a mechanism for its prevention or elimination. Radiolysis as used herein refers to high energy or ionizing radiation which causes the breakage of chemical bonds. It is known that, when high energy radiation dosage, in the order, say, of 3 megarads, is absorbed by polymeric materials, the energy is rapidly distributed through the material by the photoelectric effect, the Compton effect, and even a small amount of pair production. The energetic species formed, e.g., high energy electrons and free radicals, rapidly distribute their energy through the material, causing further ionization and bond breakage with free radical formation. While the energetic species mentioned above individually have very short half-lives and disappear very quickly, the population of free radicals formed in the polymeric material is very long-lived, sustained by the propagation reactions of the transient free radicals. In the amorphous regions of polypropylene, the free radicals rapidly quench. Inside the platelet crystals, however, limited mobility combined with efficient mechanisms of free radical stabilization leads to the storage of some of the energy absorbed by the plastic. As a consequence, free radical degradation of the polymeric material continues for years after irradiation, fed by the slow discharge of free radicals from the capacitor-like crystals. Eliminating or trapping these free radicals which do the bulk of degradation of polymeric materials is one mechanism to produce the desired stabilization.

Moreover, the degradation which accompanies and follows high energy irradiation is much worse in the presence of oxygen. Molecular oxygen is a diradical and, when a radiation-generated free radical is quenched, it is a spin-allowed process for oxygen which happens efficiently, yielding peroxy radicals. The peroxy radicals thus formed can lead to the autocatalytic free radical degradation of the material. Accordingly, free radical trapping is a desired mechanism for the stabilization of polymeric materials such as polypropylene.

If additives in the polymer can react with the radiation induced free radicals to form free radicals which are so stable that they cannot reignite the chain reaction, then these additives should stabilize the polymer to radiation. Even though mechanical properties can be maintained, phenolic stabilizers turn polypropylene very yellow after irradiation due to delocalization of the unpaired spin in the aromatic rings of the products of phenolic free radical chemistry. To eliminate this discoloration, the use of a non-aromatic system such as the hindered amines for forming a free radical trap is desirable.

There is currently much controversy as to the most important mechanisms of protection by hindered amines. Allen et al., "Interaction of a Hindered Piperidine Stabilizer with Hydroxy-Substituted Aromatic Carbonyl Compounds in the Photo-Stabilization of Polypropylene," Journal of Applied Polymer Science, volume 27, pages 2761–2772, 1982, investigated the ultraviolet stability of polypropylene containing Tinuvin 770 hindered amine (Ciba-Geigy Corporation), benzophenone derivatives, and anthraquinone derivatives as well as combinations of these materials. Different frequencies of ultraviolet energy were used and different chemistry was observed to result. Protection against near ultraviolet light (low energy) was better for Tinuvin 770 with UV 531 (2-hydroxy-4-n-octoxybenzophenone) or 1-hydroxy-anthraquinone than for Tinuvin 770 alone. Protection against the more energetic ultraviolet light was better for Tinuvin 770 with benzophenone than for Tinuvin 770 alone. Interestingly, the work of Allen et al. disclosed reversals in additive package efficacy depending upon the energy of the ultraviolet photons used. Their conclusion, that peroxide decomposition is the most important mechanism of stabilization by Tinuvin 770 to ultraviolet of wavelengths greater than 340 nm was due to the observation that Tinuvin 770 prevents polymer degradation by near UV but not by far UV (less than 340 nm). The work of Allen et al. showed that benzophenone improved stability of a T-770 mix to far UV (<340 nm) but not near UV, for which the effect was antagonistic. When 1-hydroxyanthraquinone was similarly employed with T-770 mixes, the effect of frequency was reversed. They clearly demonstrate by their work that the mechanism of polymer degradation, and thus the efficacy of candidate stabilizer packages, is dependent on the energy of the photons of irradiation. Therefore, packages which give high stability to solar radiation will not necessarily work for UV less than 340 nm or for ionizing radiation.

Other photostabilizers related to polyalkylpiperidine derivatives have been disclosed in U.S. Pat. Nos. 4,314,933 and 4,344,876. The subject matter of these two patents is related and deals with stabilizing lacquer resin against light, moisture and oxygen using any of a large variety of hindered amines. One of the listed hindered amine compounds has a 2-hydroxybenzophenone moiety. However, in U.S. Pat. No. 4,314,933, at col. 18, starting on line 30 thereof, it was pointed out that more stability to UV light can be achieved by adding UV absorbers and other conventional stabilizers. This is not a statement of synergism but merely a reiteration of a very old and understood principle of light stabilizers; the more UV excluded from the plastic, the less UV-induced degradation will occur. Not all absorbers, however, will cooperate with the hindered amine. For example, many of the organic nickel compounds suggested for use with hindered amines are hydroperoxide decomposers and, just like thioester, their addition to a hindered amine polypropylene will decrease its stability. It has been demonstrated that synergism can be achieved with some of the materials listed in U.S. Pat. No. 4,314,933, while antagonism occurs with slightly different chemicals of the same type. Thus, the patentee has made broad, general characterizations, but has failed to state a synergistic effect between the hindered amine and any specific compounds.

Carlsson et al., in the Journal of Applied Polymer Science, 16 615 (1972) includes resorcinol monobenzoate (RMB) in a list of stabilizing additives for polypropylene films. U.S. Pat. No. 3,546,161 discloses stabilization of polyolefins toward light with RMB and an alkyl amine.

Despite the aforementioned investigations and patented inventions, the unsolved problems of the radiation degradation, oxidation and stabilization of polymers still exist. It is toward the solution of these problems, or at least to an improvement thereover, that the inventive efforts of the present invention have been directed.

SUMMARY OF THE INVENTION

A radiation stabilized and sterilized flexible article comprises a semi-crystalline polymer preferably a polyolefin, having a crystalline content of from twenty percent to ninety percent. This polymer has been irradiated with a sterilizing amount of high energy radiation while having incorporated therein radiation stabilizing amounts of a hindered piperidine compound and another stabilizing additive, preferably a benzophenone precursor, sufficient to render the article substantially resistant to radiolysis while retaining its flexibility.

In another aspect of the present invention, a method for rendering semi-crystalline polymers, preferably polyolefins, radiation sterilizable includes subjecting to a sterilizing amount of high energy radiation a semi-crystalline polymer having a crystalline content of from twenty percent to ninety percent which has incorporated therein radiation stabilizing amounts of a hindered piperidine compound and another stabilizing additive sufficient to render the polymer substantially resistant to radiolysis, while retaining its flexibility.

In accordance with the principles of the present invention, polymeric materials, such as the polyolefins, and particularly, polypropylene, are sterilizable and rendered stable to high energy irradiation. The combination of a hindered piperidine and another additive, selected from the group of materials as explained below, provides a synergistic level of stabilization that the individual materials, acting alone, would not normally impart to polymeric material subjected to high doses of radiation. Post irradiative oxidation is substantially reduced in polymeric materials containing these radiation stabilizing additives. At the same time, the preferred combinations of polymer and radiation stabilizing additives not only show good resistance to post-irradiative oxidation but also resist discoloration while retaining flexibility. These features are highly advantageous, particularly when the improved polymeric materials are made into articles such as syringes, film packages and other medical products which are normally sterilized before use.

DETAILED DESCRIPTION

While this invention is satisfied by embodiments in many different forms, there will be described herein preferred embodiments of the invention, with the understanding that the present disclosure is to be considered as exemplary of the principles of the invention and is not intended to limit the invention to the embodiments illustrated. The scope of the invention will be measured by the appended claims and their equivalents.

In accordance with the present invention, the polymers employed are semi-crystalline polymers, with such polymers having a crystalline content in the order of from twenty percent to ninety percent, and preferably of from forty percent to eighty percent. The polymer may be comprised of one, two or more monomers, with the term polymer generically referring to homopolymers and to copolymers (comprised of two or more monomers). Representative examples of suitable polymers are polymers of propylene, ethylene, oxymethylene, butylene, etc., although the preferred polymer is polypropylene.

Incorporated into the polymer in radiation stabilizing amounts are two ingredients: a hindered piperidine compound and another stabilizing additive, sufficient to render the article substantially resistant to radiolysis while retaining its flexibility. Preferably, a bis(hindered piperidine) compound, most preferably a hindered bis(4-piperidinyl)diester of a dicarboxylic acid may be used in the present invention. Representative examples of bis(hindered piperidinyl)diesters acceptable for use in the present invention, but not limited thereby, are the following: bis(2,2,6,6-tetramethyl-4-piperidinyl)sebacate; bis(1,2,2,6,6-pentamethyl-4-piperidinyl)-2-n-butyl-2-(3,5-di-tert-butyl-4-hydroxybenzyl)malonate; and bis(1,2,2,6,6-pentamethyl-4-piperidinyl)sebacate. These hindered piperidines are commonly referred to as Tinuvin 770, Tinuvin 144, and Tinuvin 292, respectively, and are available from the Ciba-Geigy Corporation.

When the hindered piperidien stabilizer is incorporated into the polymer, the amounts thereof generally range from about 0.01 percent to 5.0 percent by weight and preferably from about 0.05 percent to 3.0 percent, by weight.

In addition to the hindered piperidine compound, another stabilizing additive is incorporated into the polymer, in accordance with the provisions of the present invention. This other additive may be a UV absorbing material such as benzophenone or a benzophenone derivative. Exemplary of suitable benzophenone derivatives are 4-dodecyloxy-2-hydroxybenzophenone and 2-hydroxy-4-n-octoxybenzophenone. The most preferred stabilizing additive is a benzophenone precursor, such as, for example, RMB, which under exposure to ultraviolet light, of the proper frequency, will rearrange into a benzophenone structure. In the present invention, this additive, when combined with the hindered piperidine, confers degradation stability to the polypropylene by dissipating the high energy sterilizing radiation and by decomposing harmlessly any products, such as those containing free radicals, which may be formed in the polypropylene matrix by the sterilizing radiation. It is appreciated that other benzophenone derivatives or precursors may be utilized within the purview of the present invention.

When the stabilizing additive is incorporated into the polymer, it is generally present in an amount ranging between 0.01 percent and 5.0 percent and preferably ranging between 0.05 and 3.0 percent, all by weight.

In addition to the hindered piperidine compound and the other stabilizing additive, the polymer may also include other additives which are conventionally used in the art, such as internal lubricants, antioxidants, preservatives, fillers, and the like. Specifically, one internal lubricant which is desirably used with the present invention is a metal stearate, such as sodium stearate or calcium stearate.

High energy radiation is relied upon to sterilize the articles made from the polymeric material described hereinabove. The polymer is subjected to high energy radiation by any one of a variety of sources, including cobalt 60, high energy electrons, x-rays, electron beam radiation, gamma radiation, Van de Graaff generators, neutron bombardment and the like. In general, the sterilizing radiation doses are on the order of from 0.5 to 6 megarads, with the typical dose being 1.0 to 3.5 megarads. It is understood that lower or higher doses may be employed, but generally are not required.

In accordance with the present invention, the effectiveness of the stabilizing compositions herein disclosed may be determined by two methods which depend on the well-known fact that the lower a polymer's molecular weight, the more brittle it will be. Embrittlement of a polymer resulting from radiation sterilization is caused by molecular weight decrease due to radiation-induced chain breakage leading first to peroxide intermediates and subsequently to carbonyl compounds.

Infrared measurement of the carbonyl products provides a means of measuring embrittlement and thus stability toward radiation-induced degradation. A Carbonyl Index may be determined and relied upon to rate the relative radiation stability of polymers. By using such a Carbonyl Index, simple comparison of the radiation stabilities of the various radiation grade polymers can be made. In using this Carbonyl Index, high values indicate low stability, and vice versa.

Radiation stability may also be determined by Thermogravimetric Analysis (TGA). In this procedure, a measurement is made of the rate at which a polymer decomposes into gas at 220° C. after inducing accelerated degradation by storage at 120° C. Gas formation occurs consequent to further decomposition of the above described carbonyl compounds. Thus, the more a polymer is fragmented into carbonyl compounds, the faster it turns to gas at 220° C. In the present invention, TGA may conveniently be performed using a Perkin Elmer Thermogravimetric System, model TGS-2.

The following illustrative examples are provided to exemplify the invention as described herein while not limiting the present invention to such working examples.

EXAMPLE 1

Polypropylene was mixed with 0.1% Tinuvin 770, 0.1% 4-dodecyloxy-2-hydroxybenzophenone (Eastman DOBP), and 0.1% calcium stearate. This formulation was irradiated to 5.4 megarads in air using cobalt 60, and the formulation was maintained at 60° C. After twenty-one days, the Carbonyl Index was determined to be 0.35. As a comparison, and for control purposes, a polypropylene formulation was mixed according to the above formulation but without including the Eastman DOBP. After 5.4 megarads irradiation and twenty-one days at 60° C., the Carbonyl Index for this material, without DOBP, was 0.40. The polypropylene formulation with the Tinuvin 770 and DOBP showed good resistance to post-cobalt oxidation and no discernable discoloration.

EXAMPLE 2

Polypropylene was mixed with 0.1% Tinuvin 144, 0.1% resorcinol monobenzoate (Eastman RMB), and 0.1% sodium stearate. This formulation was irradiated to 5.4 megarads using cobalt 60 in air. Following irradiation, the sample was maintained at 60° C. for twenty-one days. At that time, the Carbonyl Index was determined to be 0.30. In comparison, a polypropylene formulation was mixed with Tinuvin 144, but without the RMB. After irradiation at 5.4 megarads and twenty-one days at 60° C., its Carbonyl Index was determined to be 0.36. The polypropylene formulation with Tinuvin 144 and RMB was the most highly resistant to post-irradiative oxidation formulated in this work. It had a very small change in Carbonyl Index from 0 megarads to 5.4 megarads with zero days at 60° C., and from zero days to twenty-one days at 60° C., as well. However, this polypropylene formulation turned brown subsequent to irradiation, thus making it undesirable for many articles in the health and medical field; however, being the most stable mix made, it merits interest.

EXAMPLE 3

Polypropylene was mixed with 0.1% Tinuvin 770, 0.1% benzophenone and 0.1% sodium stearate. This formulation was irradiated to 5.4 megarads in air using cobalt 60. Following irradiation, the sample was maintained at 60° C. for twenty-one days. Thereafter, the Carbonyl Index was determined to be 0.36. No discoloration was apparent subsequent to the irradiation of this formulation.

EXAMPLE 4

Thin films were prepared from three polypropylene formulations containing 0.1% sodium stearate and the following additives:
Formulation 1: 0.1% Tinuvin 144
Formulation 2: 0.1% RMB
Formulation 3: 0.1% Tinuvin 144 and 0.1% RMB
After being subjected to about 2 megarads of colbalt radiation, the films were maintained at 120° C. for 15½ hours, cooled to room temperature for 10 hours, then maintained at 120° C. for another 11 hours. The films were placed in the TGS-2 and heated at a rate of 40° C. per minute up to 220° C., and held at that temperature while the weight of the sample was measured as a function of time. The initial rates of weight decrease were determined to be:
Formulation 1: 2.17% per minute
Formulation 2: 4.17% per minute
Formulation 3: 1.78% per minute
Formulation 3 is seen to have a level of stability substantially greater than would be expected based on the results observed for formulations 1 and 2 and clearly demonstrates a synergistic stabilizing effect between the Tinuvin 144 and RMB.

What is claimed:
1. A radiation stabilized and sterilized, flexible article comprising:
 a polyolefin having a crystalline content of from twenty percent to ninety percent;
 0.01 percent to 5.0 percent by weight of a hindered piperidine stabilizer; and
 0.01 percent to 5.0 percent by weight of resorcinol monobenzoate, said article having been irradiated with a sterilizing amount of high energy radiation and being substantially resistant to radiolysis while retaining its flexibility.
2. The article of claim 1 wherein said stabilizer is a hindered bis(4-piperidinyl)diester of a dicarboxylic acid.
3. The article of claim 2 wherein said stabilizer is bis(2,2,6,6-tetramethyl-4-piperidinyl)sebacate.
4. The article of claim 2 wherein said stabilizer is bis(1,2,2,6,6-pentamethyl-4-piperidinyl) 2-n-butyl-2-(3,5-di-tert-butyl-4-hydroxybenzyl)malonate.
5. The article of claim 2 wherein said stabilizer is bis(1,2,2,6,6-pentamethyl-4-piperidinyl)sebacate.
6. The article of claim 1 which further includes an internal lubricant.
7. The article of claim 6 wherein said lubricant is a metal stearate.
8. The article of claim 1 in the form of a syringe.
9. The article of claim 1 in the form of a package film.
10. A radiation stabilized and sterilized article comprising:
 a semi-crystalline polymer having a crystalline content of from twenty percent to ninety percent, said polymer having been irradiated with a sterilizing amount of high energy radiation while having incorporated therein radiation stabilizing amounts of a hindered piperidine compound and resorcinol monobenzoate sufficient to render said article substantially resistant to radiolysis.
11. A radiation stabilized and sterilized, flexible article comprising:
 a polyolefin having a crystalline content of from twenty percent to ninety percent;
 0.01 percent to 5.0 percent by weight of a hindered bis(4-piperidinyl)diester of a dicarboxylic acid; and
 0.01 percent to 5.0 percent by weight of resorcinol monobenzoate, said article having been irradiated with a sterilizing amount of high energy radiation and being substantially resistant to radiolysis while retaining its flexibility.
12. A method for sterilizing and radiation stabilizing a polyolefin comprising:
 subjecting a polyolefin to a sterilizing amount of high energy radiation, said polyolefin having a crystalline content of from twenty percent to ninety percent and having incorporated therein 0.01 percent to 5.0 percent by weight of a hindered piperidine stabilizer and 0.01 percent to 5.0 percent by weight of resorcinol monobenzoate to thereby produce a polyolefin which is substantially resistant to radiolysis while retaining its flexibility.
13. The method in accordance with claim 12 wherein said stabilizer is a hindered bis(4-piperidinyl)diester of a dicarboxylic acid.
14. The method of claim 12 wherein said polyolefin is in the form of an article.
15. The method of claim 12 wherein said polyolefin is subjected to high energy radiation ranging between 0.5 and 6 megarads.
16. The method of claim 13 wherein said stabilizer is bis(2,2,6,6-tetramethyl-4-piperidinyl) sebacate.
17. The method of claim 13 wherein the stabilizer is bis(1,2,2,6,6-pentamethyl-4-piperidinyl)-2-n-butyl-2-(3,5-di-tert-butyl-4-hydroxybenzyl)malonate.
18. The method of claim 13 wherein the stabilizer is bis(1,2,2,6,6-pentamethyl-4-piperidinyl)sebacate.
19. The method of claim 12 which further includes the addition of an internal lubricant.
20. A method for rendering semi-crystalline polymers radiation sterilizable comprising:
 subjecting to a sterilizing amount of high energy radiation a semi-crystalline polymer having a crystalline content of from twenty to ninety percent and having incorporated therein radiation stabilizing amounts of a hindered piperidine compound and resorcinol monobenzoate sufficient to render said polymer substantially resistant to radiolysis and post-irradiative oxidative degradation.

21. A method for sterilizing and radiation stabilizing a polyolefin comprising:
subjecting a polyolefin to a sterilizing amount of high energy radiation, said polyolefin having a crystalline content of from twenty percent to ninety percent and having incorporated therein 0.01 percent to 5.0 percent by weight of a hindered bis(4-piperidinyl)diester of dicarboxylic acid and 0.01 percent to 5.0 percent by weight of resorcinol monobenzoate to thereby produce a polyolefin which is substantially resistant to radiolysis while retaining its flexibility.

* * * * *